United States Patent
Lee et al.

(10) Patent No.: US 9,372,165 B2
(45) Date of Patent: Jun. 21, 2016

(54) GAS SENSOR AND METHOD OF MANUFACTURING THE SAME

(75) Inventors: Hyung Kun Lee, Daejeon (KR); Woo Seok Yang, Daejeon (KR); Nak Jin Choi, Daejeon (KR); Seung Eon Moon, Daejeon (KR); Jong Dae Kim, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 727 days.

(21) Appl. No.: 13/593,771

(22) Filed: Aug. 24, 2012

(65) Prior Publication Data

US 2013/0091929 A1   Apr. 18, 2013

(30) Foreign Application Priority Data

Oct. 13, 2011   (KR) .................. 10-2011-0104493

(51) Int. Cl.
*G01N 27/18* (2006.01)
*G01N 27/12* (2006.01)
*B82Y 15/00* (2011.01)

(52) U.S. Cl.
CPC .............. *G01N 27/18* (2013.01); *B82Y 15/00* (2013.01); *G01N 27/126* (2013.01); *G01N 27/127* (2013.01)

(58) Field of Classification Search
CPC ..... B82Y 15/00; G01N 27/127; G01N 27/14; G01N 24/18
See application file for complete search history.

(56) References Cited

U.S. PATENT DOCUMENTS

| | | | | |
|---|---|---|---|---|
| 4,126,758 A | * | 11/1978 | Krumme | 174/553 |
| 4,967,589 A | * | 11/1990 | Yagawara et al. | 73/23.25 |
| 5,031,821 A | * | 7/1991 | Kaneda et al. | 228/110.1 |
| 5,841,021 A | | 11/1998 | De Castro | |
| 5,942,676 A | * | 8/1999 | Potthast et al. | 73/31.06 |
| 5,983,734 A | * | 11/1999 | Mathur et al. | 73/864.24 |
| 6,997,040 B1 | * | 2/2006 | Lee et al. | 73/31.05 |
| 7,866,202 B2 | * | 1/2011 | Chen et al. | 73/31.06 |
| 8,257,605 B2 | * | 9/2012 | Kobayashi et al. | 216/91 |
| 8,915,121 B2 | * | 12/2014 | Kumar et al. | 73/31.03 |
| 2002/0132389 A1 | * | 9/2002 | Patel et al. | 438/97 |
| 2004/0159837 A1 | * | 8/2004 | Inoue | 257/59 |
| 2005/0006236 A1 | * | 1/2005 | Kim et al. | 204/415 |
| 2005/0167400 A1 | * | 8/2005 | Wurzbacher et al. | 216/87 |
| 2006/0049049 A1 | | 3/2006 | Scheer et al. | |
| 2010/0078808 A1 | * | 4/2010 | Burch et al. | 257/723 |
| 2010/0294024 A1 | * | 11/2010 | Kumar et al. | 73/38 |

FOREIGN PATENT DOCUMENTS

JP   2000-137017 A   5/2000

OTHER PUBLICATIONS

English Language Translation of JP 2000-137017, Detailed Description, pp. 1-8, obtained on Nov. 3, 2015 at < https://www.j-platpat.inpit.go.jp/web/all/top/BTmTopEnglishPage>.*
Jianwei Gong et al., "Micromachined nanocrystalline silver doped SnO2 H2S sensor", Sensors and Actuators, 2006, pp. 32-39, B 114.

* cited by examiner

*Primary Examiner* — Lisa Caputo
*Assistant Examiner* — Punam Roy

(57) ABSTRACT

Disclosed are a gas sensor, and a method of manufacturing and using the same. The method includes: forming a detection material on a heater; coating an encapsulant on the detection material; and heating the heater to remove the encapsulant from the detection material when the gas sensor is operated.

9 Claims, 4 Drawing Sheets

GAS SENSOR AND METHOD OF MANUFACTURING THE SAME

CROSS-REFERENCE TO RELATED APPLICATIONS

This application is based on and claims priority from Korean Patent Application No. 10-2011-0104493, filed on Oct. 13, 2011, with the Korean Intellectual Property Office, the disclosure of which is incorporated herein in its entirety by reference.

TECHNICAL FIELD

The present disclosure relates to a gas sensor, and more particularly, to a gas sensor for preventing an electrical property thereof from being changed by toxic gases, moisture or UV rays when the gas sensor is stored for a long time, and a method of manufacturing and using the same.

BACKGROUND

A semiconductor gas sensor is operated to determine a concentration of a detection gas by using a degree by which a resistance of a detection material such as a metal oxide, a polymer and a carbon nano tube is changed during an oxidation/reduction reaction of the detection gas and the detection material. To this end, the semiconductor gas sensor employs a dedicated heater for a smooth oxidation/reduction reaction of a detection gas and a detection material, and such a reaction is generated in a temperature section of 200 to 500 degrees Celsius.

An electrochemical gas sensor is operated to determine a concentration of a gas through a degree by which a current or an electromotive force is changed while the detection gas and a detection material such as an alkaline metal or an alkaline earth metal carbonate react each other at a high temperature to influence an ion conductivity of a solid electrolyte.

The semiconductor gas sensor or the electrochemical gas sensor employs a heater therein in terms of operation principle. The detection material used for the semiconductor gas sensor or the electrochemical gas sensor mainly includes a metal oxide, an alkaline metal carbonate, a carbon nano tube, graphene or a polymer.

However, a gas sensor according to the related art is known that sensitivity, selectivity and the like are influenced by humidity, that is, water molecules in the air (Jianwei Gong et al., Sensors and Actuators B 114(2006) 32-39). To solve this problem, a study for improving humidity stability of a gas sensor through a filter for adsorbing moisture to a gas inlet port or removing moisture from the gas inlet port while the gas sensor is packaged (U.S. Pat. No. 5,841,021). Such a filter technology helps remove moisture of a part of a gas sensor and secure stability of the gas sensor, deteriorates efficiency of the gas sensor in a situation where excessive moisture is present. And the filter has a limit in life when the filter is stored for a long time. Therefore, a process of replacing a filter after a predetermined time period is required to protect a gas sensor.

SUMMARY

The present disclosure has been made in an effort to provide a gas sensor for preventing an electrical property thereof from being changed by toxic gases, moisture or UV rays when the gas sensor is stored for a long time, and a method of manufacturing and using the same.

An exemplary embodiment of the present disclosure provides a gas sensor including: a heater; a detection material formed on the heater; and an encapsulant sealing the detection material.

Another exemplary embodiment of the present disclosure provides a method of manufacturing and using a gas sensor, including: forming a detection material on a heater; coating an encapsulant on the detection material; and heating the heater to remove the encapsulant from the detection material when the gas sensor is operated.

According to the exemplary embodiments of the present disclosure, by providing a gas sensor which coats a detection material with an encapsulant and removes the encapsulant from a detection material by using a heater installed therein shortly before the gas sensor is used, and a method of manufacturing and using the same, it is possible to secure stability during storage of the gas sensor, and to effectively utilize the gas sensor while excluding a poisoning phenomenon due to a long time storage of the gas sensor.

Further, according to the exemplary embodiments of the present disclosure, it is possible to replace a poisoned gas sensor and operate a reliable sensor node by providing a gas sensor which removes an encapsulant of a preliminary gas sensor by using a heater installed therein according to an encapsulant thermal decomposition command or an algorithm for removing the encapsulant from a server if a poisoning phenomenon of a gas sensor in operation is detected when a plurality of preliminary gas sensors are stored at sensor nodes by using an encapsulant, and a method of manufacturing and using the same.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

In the following detailed description, reference is made to the accompanying drawing, which form a part hereof. The illustrative embodiments described in the detailed description, drawing, and claims are not meant to be limiting. Other embodiments may be utilized, and other changes may be made, without departing from the spirit or scope of the subject matter presented here.

Hereinafter, exemplary embodiments of the present disclosure will be described in detail with reference to the accompanying drawings. In describing the present disclosure, a detailed description of related known configurations and functions will be omitted when it may make the essence of the present disclosure obscure.

Figure 1:
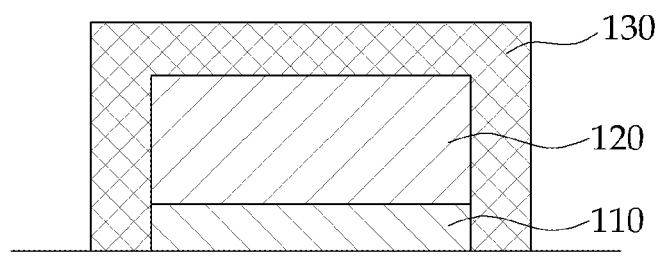
FIG. 1 is a sectional view illustrating a structure of a gas sensor according to an exemplary embodiment of the present disclosure.

FIG. 1 is a sectional view illustrating a structure of a gas sensor according to an exemplary embodiment of the present disclosure.

Referring to FIG. 1, a gas sensor according to the present disclosure includes a heater 110, a detection material 120, an encapsulant 130, and the like. Here, the gas sensor may be a semiconductor gas sensor, an electrochemical gas sensor or the like.

The heater 110 is an alumina heater, and generates heat by using a voltage and a current applied thereto. The heater 110 according to the present disclosure may be used to coat the encapsulant 120 on the detection material 120 or to remove the encapsulant 130 from the detection material 120.

The detection material 120 is formed on the heater 110 and is $SnO_2$. Here, the detection material 120 detects the detection gas through a change in resistance, current, electromotive force or the like.

The encapsulant 130 is coated on the detection material to protect the detection material 120 from toxic gases, moisture, oxygen, UV rays and the like. Here, the encapsulant 130 is formed in the form of a film having a thickness of 100 to 200 μm.

The encapsulant 130 may be any one of a polymer such as poly(vinyl alcohol-co-ethylene), poly(vinylidene difluoride), poly(vinylidene dichloride), poly(vinylidene chloride-co-methylacrylate) and the like and inorganic particles such as aluminum oxide, silicon oxide, silicon nitride, aluminosilicate, metal nanoparticles, quantum dots, and the like, or a combination thereof.

Thus, when the gas sensor according to the present disclosure is operated, the heater 110 may be heated to a thermal decomposition temperature of the encapsulant 130 or higher to thermally decompose the encapsulant 130 while removing the encapsulant 130 from the detection material 120. Accordingly, the detection material 120 is exposed to the detection gas such that the gas sensor is operated.

Figure 2:
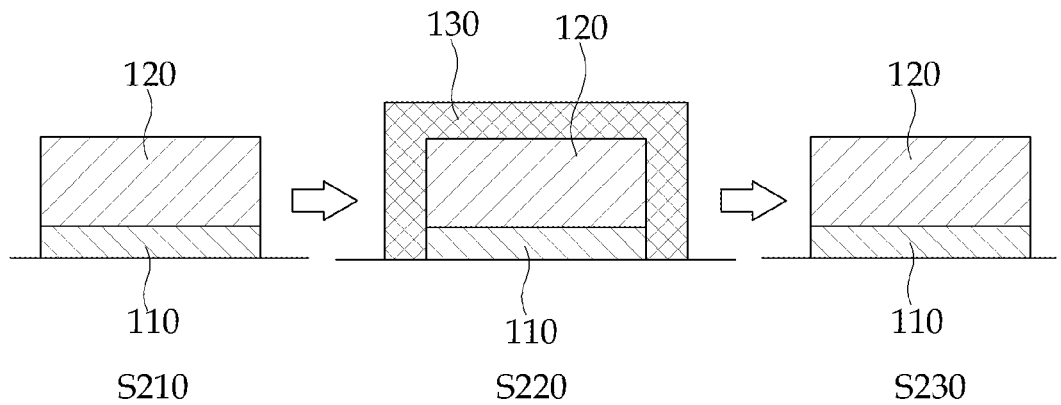
FIG. 2 is a process flowchart illustrating a method of manufacturing and using a gas sensor according to an exemplary embodiment of the present disclosure.

FIG. 2 is a process flowchart illustrating a method of manufacturing and using a gas sensor according to an exemplary embodiment of the present disclosure.

Referring to FIG. 2, the detection material 120 is formed on the heater 110 through screen printing (S210).

Next, the encapsulant 130 is coated on the detection material 120 through a method such as pressing, thermocompression binding, spin coating, drop coating, dip coating, spray coating, and the like (S220). In this case, when the encapsulant 130 is coated through thermocompression binding, the encapsulant 130 may be heated to a glass transition temperature or higher (for example, 150 to 170 degrees Celsius) to be coated by using an external heater or an embedded heater 110 having therein. When the encapsulant 130 is coated through pressing or thermocompression binding, an encapsulant 130 in the form of a film having a thickness of 100 to 200 μm may be used.

When an operation of the gas sensor is required to detect a gas after the gas sensor is stored, the heater 110 is heated to a thermal decomposition temperature of the encapsulant 130 or higher (for example, 550 degrees Celsius) to thermally decompose the encapsulant 130 while removing the encapsulant 130 from the detection material 120 (S230). Accordingly, the detection material 120 is exposed to the detection gas such that the gas sensor is operated.

Figure 3:
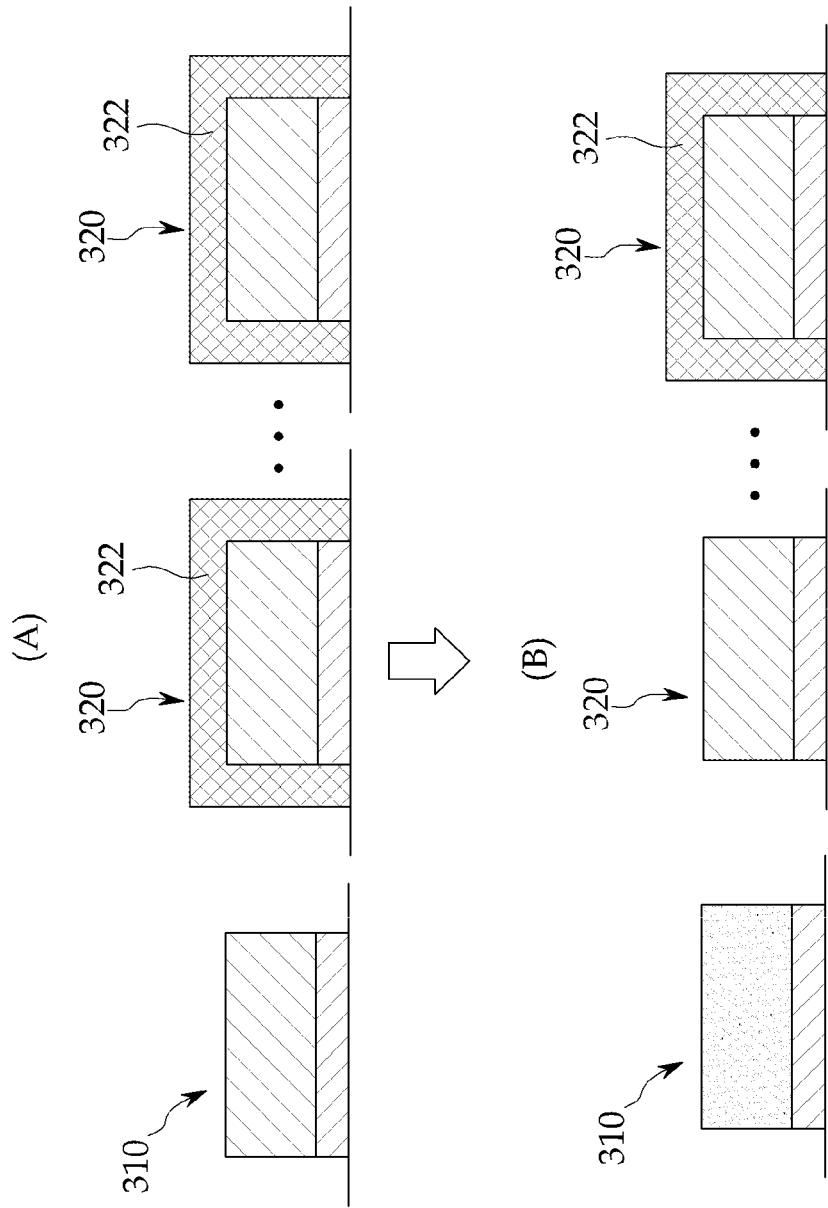
FIG. 3 is a view illustrating an application example of a gas sensor according to an exemplary embodiment of the present disclosure.

FIG. 3 is a view illustrating an application example of a gas sensor according to an exemplary embodiment of the present disclosure.

A plurality of the gas sensors according to the present disclosure may be installed wirelessly or through wires in various environments for the purpose of monitoring the environments in measurement spaces. When the detection materials of the gas sensors are poisoned by toxic gases, moisture, UV rays and the like in such environments, the gas sensors may not be normally operated to fail to effectively monitor atmospheric environment information in the measurement spaces, acting as a serious failure factor of the entire atmosphere monitoring system.

Accordingly, as illustrated in FIG. 3A, a plurality of gas sensors 320 are preliminarily mounted to sensor nodes, and the sensor nodes are sealed by encapsulants 322 to be protected from a poisoning factor in a measurement space.

As illustrated in FIG. 3B, when the gas sensor 310 in operation is poisoned to show an abnormal behavior, one encapsulant 322 is removed from the preliminary gas sensor 310 according to an encapsulant thermal decomposition command or an algorithm for removing the encapsulant from a server to operate the gas sensor 310.

Figure 4:
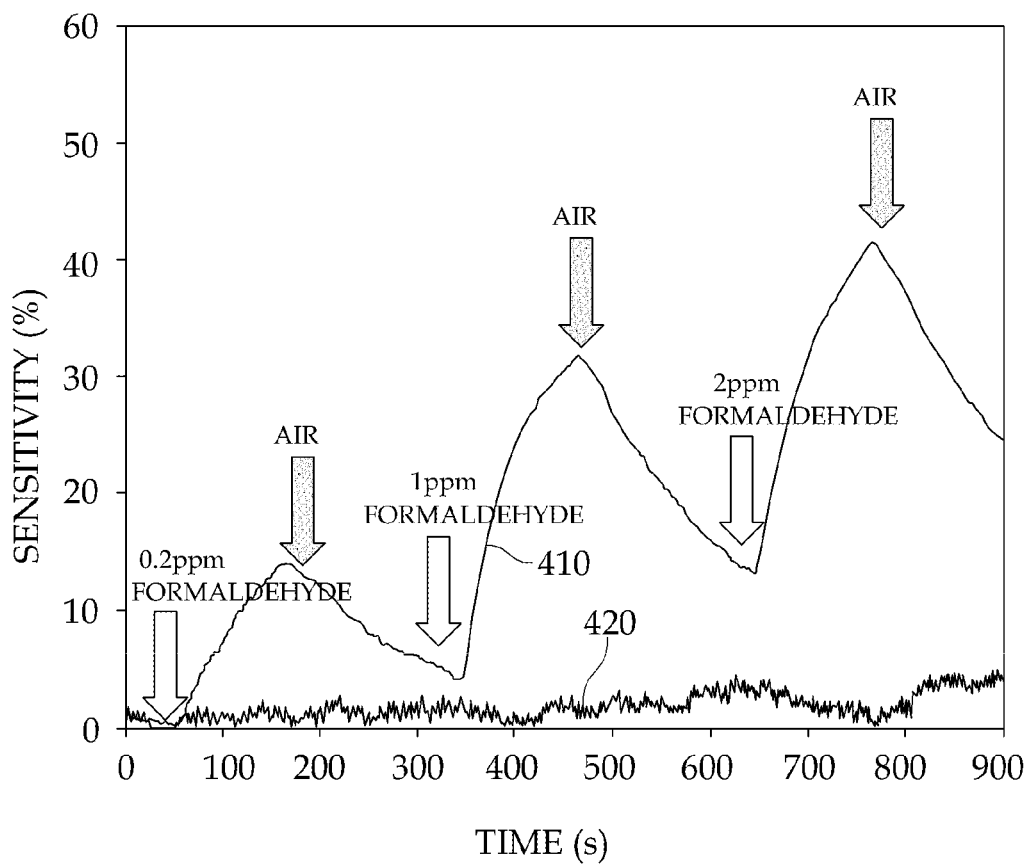
FIG. 4 is a graph for comparing detection characteristics of a general gas sensor and a gas sensor sealed by an encapsulant to formaldehyde.

FIG. 4 is a graph for comparing detection characteristics of a general gas sensor and a gas sensor sealed by an encapsulant to formaldehyde.

When a sensor resistance in an environment without formaldehyde is Ra and a sensor resistance during a measurement of formaldehyde is Rg, a sensitivity (%) of a gas sensor is defined as $|Ra-Rg|/Ra*100$.

As illustrated in FIG. 4, it can be seen that, in the case of a gas sensor 410 where a detection material is not sealed by an encapsulant, sensitivity is changed from 10% to 45% under a condition where formaldehyde of 0.2 ppm to 2 ppm is present.

It can be also seen that, in a gas sensor 420 where a detection material is sealed by an encapsulant, sensitivity is a value ranging from 0 to 5% regardless of a concentration of formaldehyde. Through this, it can be seen that an encapsulant protects a detection material from an exterior toxic gas.

Figure 5:
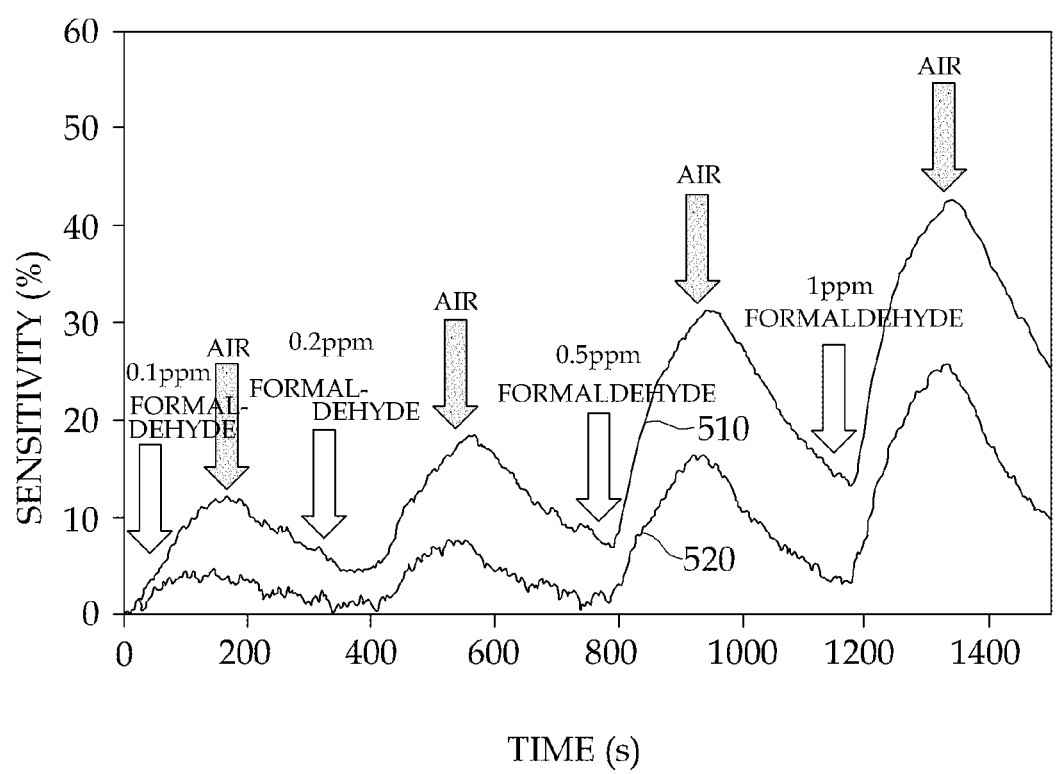
FIG. 5 is a graph for comparing detection characteristics of a general gas sensor and a gas sensor from which an encapsulant is removed to formaldehyde.

FIG. 5 is a graph for comparing detection characteristics of a general gas sensor and a gas sensor from which an encapsulant is removed to formaldehyde.

Referring to FIG. 5, it can be seen that, in the case of a gas sensor 520 from which an encapsulant is removed, a general gas sensor 510 does not react formaldehyde at all when sealed by an encapsulant, whereas the gas sensor 520 shows a sensitivity performance of approximately ½ of that of the general gas sensor 510 after encapsulant is removed. The sensitivity performance is a level which does not matter at all in the gas sensor detecting formaldehyde.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A gas sensor comprising:
    a heater;
    a detection material disposed on the heater; and
    an encapsulant disposed on the detection material and sealing the detection material from a detected gas,
    wherein the heater is operable to heat the encapsulant, and
    wherein the detection material includes $SnO_2$ and contacts a top surface of the heater.

2. A method of manufacturing and using a gas sensor, the method comprising:

forming a detection material on a heater;
coating an encapsulant on the detection material; and
heating the heater to remove the encapsulant from the detection material when the gas sensor is operated.

3. The method of claim 2, wherein in the forming of the detection material, the detection material is formed on the heater through screen printing.

4. The method of claim 2, wherein in the coating of the encapsulant, the encapsulant is coated on the detection material through any one process of pressing, thermocompression binding, spin coating, drop coating, dip coating and spray coating.

5. The method of claim 2, wherein in the coating of the encapsulant, the encapsulant is heated by an external heat source or the heater to be coated on the detection material.

6. The method of claim 5, wherein the encapsulant is heated to a temperature in a range from 150 to 170° C.

7. The method of claim 2, wherein in the removing of the encapsulant, when the gas sensor is operated, the encapsulant is removed from the detection material by heating the heater to a thermal decomposition temperature of the encapsulant or higher.

8. The method of claim 2, wherein the gas sensor is a first gas sensor that includes the heater, the detection material, and the encapsulant, the method further comprising:
    detecting an abnormal operation of the first gas sensor; and
    heating a heater of a second gas sensor and removing an encapsulant of the second gas sensor, when the abnormal operation of the first gas sensor is detected.

9. A gas sensor comprising:
a heater;
a detection material disposed on the heater; and
an encapsulant disposed on the detection material and sealing the detection material from a detected gas,
wherein the heater is operable to heat the encapsulant, and
wherein the encapsulant directly contacts the heater.

* * * * *